(12) United States Patent
Saito

(10) Patent No.: US 10,234,281 B2
(45) Date of Patent: Mar. 19, 2019

(54) METHOD FOR EVALUATING HAZE

(71) Applicant: SHIN-ETSU HANDOTAI CO., LTD., Tokyo (JP)

(72) Inventor: Hisayuki Saito, Shirakawa (JP)

(73) Assignee: SHIN-ETSU HANDOTAI CO., LTD., Tokyo (JP)

( * ) Notice: Subject to any disclaimer, the term of this patent is extended or adjusted under 35 U.S.C. 154(b) by 0 days.

(21) Appl. No.: 15/570,278

(22) PCT Filed: Mar. 10, 2016

(86) PCT No.: PCT/JP2016/001315
§ 371 (c)(1),
(2) Date: Oct. 27, 2017

(87) PCT Pub. No.: WO2016/181592
PCT Pub. Date: Nov. 17, 2016

(65) Prior Publication Data
US 2018/0128606 A1 May 10, 2018

(30) Foreign Application Priority Data
May 13, 2015 (JP) .................................. 2015-98286

(51) Int. Cl.
*G01B 11/30* (2006.01)
*G01N 15/14* (2006.01)

(52) U.S. Cl.
CPC ............ *G01B 11/30* (2013.01); *G01B 11/303* (2013.01); *G01N 15/14* (2013.01); *G01N 2015/1486* (2013.01)

(58) Field of Classification Search
CPC . G01B 11/30; G01N 15/14; G01N 2015/1486
(Continued)

(56) References Cited

U.S. PATENT DOCUMENTS 5,198,869 A 3/1993 Monteverde et al.
5,599,464 A 2/1997 Laird et al.
(Continued)

FOREIGN PATENT DOCUMENTS

| JP | 2007-114183 A | 5/2007 |
| JP | 3919854 B2 | 5/2007 |
| JP | 2010-109257 A | 5/2010 |

OTHER PUBLICATIONS

Oct. 24, 2017 Office Action issued in Japanese Patent Application No. 2015-098286.
(Continued)

*Primary Examiner* — Sunghee Y Gray
(74) *Attorney, Agent, or Firm* — Oliff PLC

(57) ABSTRACT

A method for evaluating a haze of a substrate surface by a particle counter apparatus using scattering light, the method including calibrating a haze value with the use of a standard sample at the time of obtaining the haze value of the substrate surface from scattering light intensity of light which is entered on the substrate surface, and by using a sample having standard particles applied thereto as the standard sample. Consequently, the method for evaluating a haze by which a haze value of the particle counter apparatus can be calibrated with the use of the standard sample for a haze and a measurement accuracy of the haze can be improved.

2 Claims, 4 Drawing Sheets

(58) Field of Classification Search
USPC .......................................................... 356/600
See application file for complete search history.

(56) References Cited

U.S. PATENT DOCUMENTS

| | | | |
|---|---|---|---|
| 6,335,269 B1* | 1/2002 | Sato | H01L 21/02381 |
| | | | 257/E21.102 |
| 8,675,182 B2* | 3/2014 | Bamji | G01S 7/497 |
| | | | 356/3.01 |
| 2007/0019188 A1* | 1/2007 | Nolot | C23C 16/44 |
| | | | 356/243.4 |
| 2011/0276299 A1 | 11/2011 | Nemoto et al. | |

OTHER PUBLICATIONS

Nov. 14, 2017 International Preliminary Report on Patentability issued in International Patent Application No. PCT/JP2016/001315.
Holsteyns et al., "Monitoring and Qualification Using Comprehensive Surface Haze Information," IEEE International Symposium on Semiconductor Manufacturing, 2003, pp. 378-381.
May 24, 2016 International Search Report issued in International Patent Application No. PCT/JP2016/001315.

* cited by examiner (a)

EXAMPLE OF APPLICATION
OF STANDARD PARTICLES (b)

SIZE/SCATTERING LIGHT
INTENSITY

MEASUREMENT RESULT OF
WAFER IN (a)

(a) HAZE MAP (b) HAZE INTENSITY DISTRIBUTION

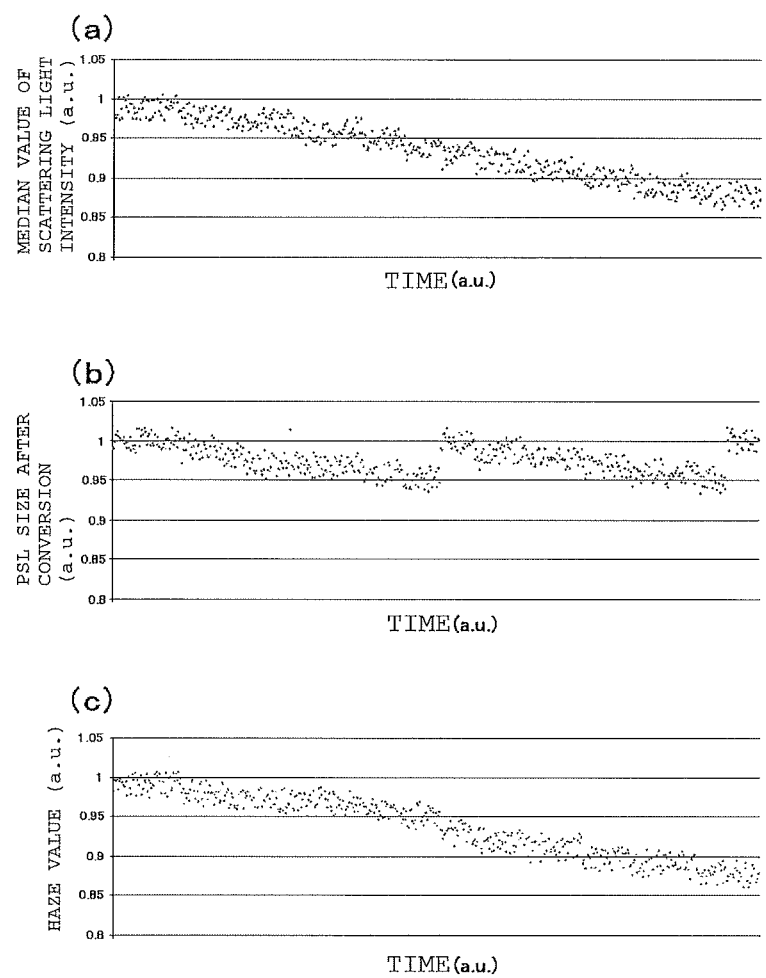

METHOD FOR EVALUATING HAZE

TECHNICAL FIELD

The present invention relates to a method for evaluating a haze.

BACKGROUND ART

In a particle counter apparatus, it is possible to perform not only particle measurement but also haze measurement. Here, the particle counter apparatus is an apparatus which checks the number or positions of particles by generating intensive scattering light when incident light strikes on a wafer and the particles are present there.

When a haze (roughness on a surface) is present on a silicon wafer surface, weak scattering light is generated by applying the light to the wafer, and hence the haze can be measured by using the particle counter apparatus.

The haze is an important quality item, and it is managed as a haze value by the particle counter apparatus. A high haze value means large roughness on a surface, and a low haze value means small roughness on the surface.

To enhance a measurement accuracy, the particle counter apparatus usually calibrates a particle size with a standard wafer (a standard sample) having standard particles (made of polystyrene or $SiO_2$) applied thereto.

Since laser intensity or sensitivity of a photomultiplier (a photomultiplier tube) slightly differs depending on each apparatus, intensity of scattering light from particles of a given fixed size is supposed to be the same with respect to the incident light, but perfectly equalizing detector sensitivity and the like is difficult, and a difference between apparatuses is filled by, in reality, placing the standard particles of a given fixed size on a wafer and treating intensity of scattering light generated from this wafer (which differs depending on each apparatus) as intensity of scattering light relative to particles of a fixed size, which is an inherent value of each apparatus.

Although the haze value should be likewise calibrated on the standard wafer (the standard sample), what are required for the standard wafer for a haze are as follows.

1) Roughness is fixed without a radial distribution, and it is fixed as seen from all directions (although an atomic step is inappropriate since a step can be seen from a given direction but no step can be seen from another direction).

2) No contamination must be produced during measurement (the haze value changes when contamination is produced).

3) No contamination or no tarnish must be produced during storage (the haze value changes when the tarnish is produced).

Patent Document 1 discloses that a standard wafer for a haze is formed by forming cylindrical irregularities on a silicon wafer surface in terms of roughness which is fixed as seen from all directions.

CITATION LIST

Patent Literature

Patent Document 1: Japanese Patent No. 3919854

DISCLOSURE OF INVENTION

Problem to be Solved by the Invention

However, as described above, the quality required for the standard sample for a haze is very difficult, and a storage method must be also considered particularly if aging is to be grasped.

Thus, forming the long-lasting standard sample for a haze is difficult, and even the standard sample for a haze disclosed in Patent Literature 1 has a problem of aging.

Further, in recent years that a request for management of a haze is growing, creating the standard sample for a haze, obtaining a difference between apparatuses, and managing aging are demanded.

In view of the problem, it is an object of the present invention to provide a method for evaluating a haze by which a haze value of a particle counter apparatus is calibrated by using a standard sample for a haze to improve a measurement accuracy of a haze.

Means for Solving Problem

In order to achieve the object, the present invention provides a method for evaluating a haze of a substrate surface by a particle counter apparatus using scattering light, the method including calibrating a haze value with the use of a standard sample at the time of obtaining the haze value of the substrate surface from scattering light intensity of light which is entered on the substrate surface, and by using a sample having standard particles applied thereto as the standard sample.

As described above, at the time of obtaining the haze value of the substrate surface from the scattering light intensity of the light which is entered on the substrate surface, the haze value is calibrated by using the standard sample, and the sample having the standard particles applied thereto is used as the standard sample, thereby improving a measurement accuracy of the haze.

At this time, it is preferable that the haze value is obtained by monitoring aging of the scattering light intensity of the light which is entered on a surface of the standard sample, and by changing a conversion rate of the haze value based on a change rate of the scattering light intensity of the standard sample.

When the haze value is obtained in this manner, the measurement accuracy of the haze can be effectively improved.

At this time, it is preferable to calibrate the haze values of a plurality of particle counter apparatuses by measuring the scattering light intensity of the standard sample by the plurality of particle counter apparatuses, and by determining a correction coefficient of the haze value based on measured values of the scattering light intensity of the standard sample.

When the haze values of the plurality of particle counter apparatuses are calibrated in this manner, the measurement accuracy for the haze when the plurality of particle counter apparatuses are used can be improved.

Effect of the Invention

As described above, according to the present invention, at the time of obtaining the haze value of the substrate surface from the scattering light intensity of the light which is entered on the substrate surface, the haze value is calibrated by using the standard sample, and the sample having the standard particles applied thereto is used as the standard sample, thereby improving the measurement accuracy of the haze.

BRIEF DESCRIPTION OF DRAWINGS

FIG. 4 is a view showing a median value of scattering light intensity, a PSL size after conversion, and aging of a haze value.

BEST MODE(S) FOR CARRYING OUT THE INVENTION

As described above, since quality required for a standard sample for a haze is very rigorous and a storage method must be taken into account particularly if aging is to be grasped, forming the standard sample for a haze which can be used for a long time is difficult, and even if such a standard sample for a haze as disclosed in Patent Document 1 is used, there is a problem of aging.

Thus, the present inventor has conducted the earnest examinations about a method for evaluating a haze by which a haze value of a particle counter apparatus can be calibrated by using the standard sample for a haze to improve a measurement accuracy of the haze. As a result, the present inventor has found out that the essence of haze measurement lies in how much the apparatus can capture scattering light relative to incident light and that a cause of production of scattering light does not have to be roughness of a substrate surface if the fixed scattering light is produced, namely, the standard sample having standard particles which reflect the fixed scattering light relative to the incident light applied thereto is applicable to not only calibration of the particles but also calibration of the haze.

Further, based on the knowledge, the present inventor has also found out that, at the time of obtaining a haze value of the substrate surface from scattering light intensity of light which is entered on the substrate surface, calibrating the haze value with the use of the standard sample and using a sample having the standard particles applied thereto as a standard sample enable improving a measurement accuracy of the haze, thereby bringing the present invention to completion.

An embodiment of the present invention will now be described hereinafter in detailed with reference to the drawings, but the present invention is not restricted thereto.

First, a method for evaluating a haze according to the present invention will be described with reference to FIG. 1.

Figure 1:
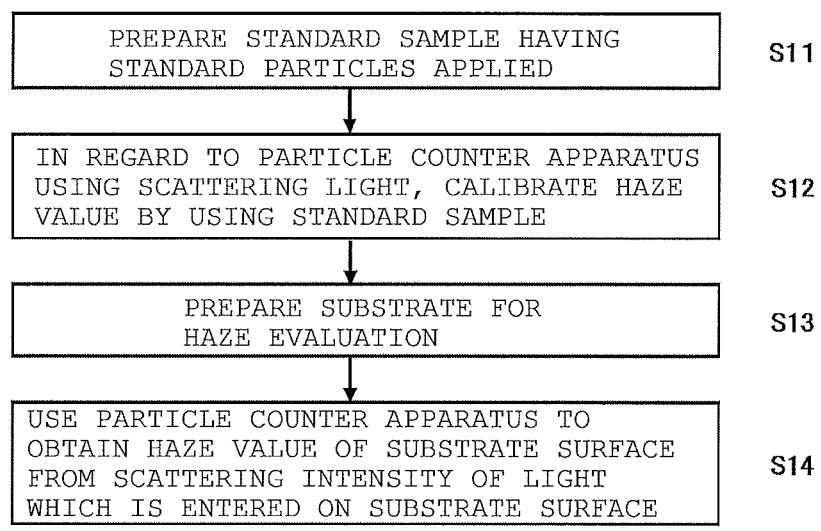
FIG. 1 is a view showing a flow of a method for evaluating a haze according to the present invention.

First, a standard sample having standard particles applied thereto is prepared (see S11 in FIG. 1).

Specifically, the standard sample having the standard particles, which have a predetermined size (a particle diameter) and are made of polystyrene (PSL), $SiO_2$, or the like, applied thereto is prepared.

Subsequently, in regard to a particle counter apparatus using scattering light, a haze value is calibrated by using the standard sample (see S12 in FIG. 1).

Specifically, the standard sample prepared at S11 is measured by the particle counter apparatus to obtain a median value (a median) of actual scattering light intensity. At this time, a measurement value must be an actually measured value of the scattering light intensity rather than a calibrated value with the use of a particle size.

The median value of the measured actual scattering light intensity is compared with a median value which is an initial value of the actual scattering light intensity when the standard sample is formed (which will be referred to as a "standard value" hereinafter), and the haze value is calibrated based on a deviation from the standard value.

In this case, when the standard sample is contaminated, an average value of the scattering light intensity varies, but the median value from the sample having the particles of a fixed size does not vary. Thus, fluctuations due to the contamination of the standard sample can be reduced.

Likewise, even if the standard sample is slightly hazy, the actual scattering light intensity from a position to which the standard particles are not attached is affected, but the actual scattering light intensity from the standard particles are hardly affected. That is because the scattering light from the standard particles is higher than the scattering light due to the haze.

Subsequently, a substrate for haze evaluation is prepared (see S13 in FIG. 1).

Specifically, a wafer in a manufacturing process in which haze management is performed is prepared.

Then, a haze value of a substrate surface is obtained from scattering intensity of the light which is entered on the substrate surface by using the particle counter apparatus (see S14 in FIG. 1).

Specifically, the haze value of the substrate surface is obtained from the scattering intensity of the light which is entered on a surface of the wafer prepared at S13 by using the particle counter apparatus by which the haze value has been calibrated at S12.

Figure 3:
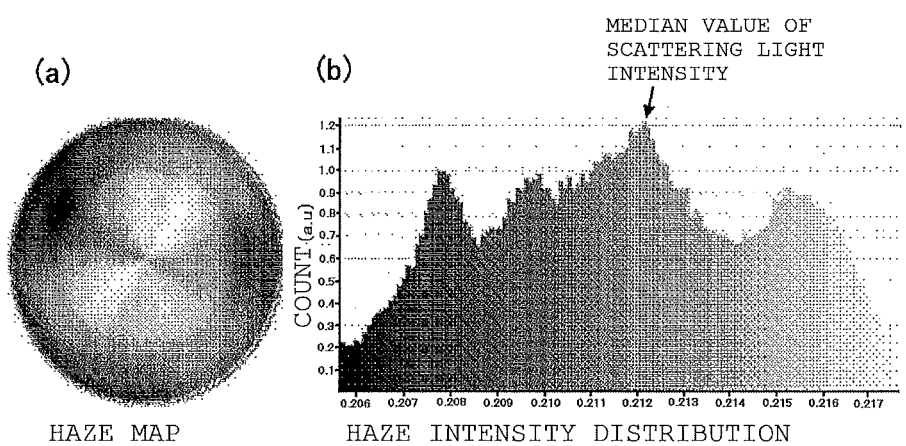
FIG. 3 is a view showing a measurement example of a haze.

Here, FIG. 3 shows a measurement example of the haze. FIG. 3(a) shows a haze map, and shows a radial distribution of the haze in the wafer. In FIG. 3(a), a light region is a region having a large haze value (large irregularities on the surface), and a dark region is a region with a small haze value (small irregularities on the surface). FIG. 3(b) shows a haze value distribution, where an axis of abscissa represents a haze value and an axis of ordinate represents a count number. It is to be noted that, in FIG. 3(b), a portion pointed by an arrow corresponds to the median value of the scattering light intensity.

Figure 2:
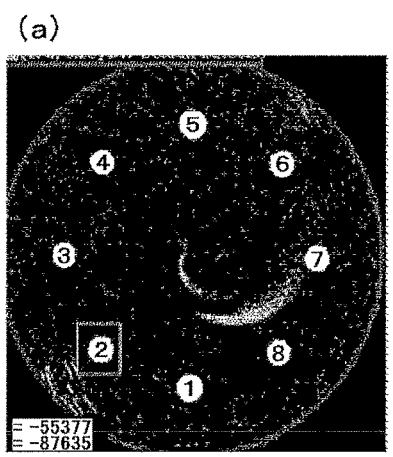
FIG. 2 is a view showing an application example of standard particles and a measurement result of a wafer having the standard particles applied thereto in this manner.
Figure 2:
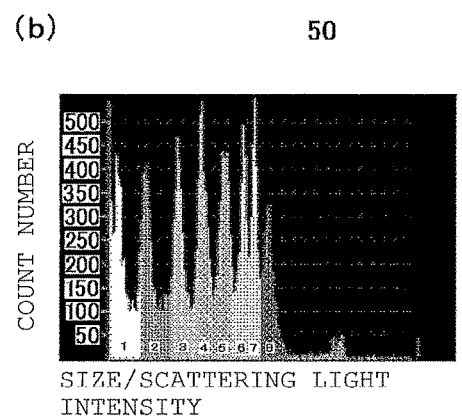

FIG. 2(a) shows an application example of the standard particles. In FIG. 2(a), the standard particles of eight different sizes are applied to an upper side of the silicon wafer. FIG. 2(b) shows a measurement result of the wafer shown in FIG. 2(a) using the particle counter apparatus. In FIG. 2(b), an axis of abscissa represents scattering light intensity (scattering light intensity produced from one standard particle) which can be converted into a particle size, and an axis of ordinate represents a count number (the number of times of production of the scattering light) which is the number of particles. It can be understood from the measurement result of FIG. 2(b) that there are eight peaks in accordance with the respective particle sizes.

When the wafer shown in FIG. 2(a) is used as the standard sample, eight types of scattering light intensity can be calibrated at the same time, and highly accurate calibration can be efficiently performed.

As described above, at the time of obtaining the haze value of the substrate surface from the scattering light intensity of the light which is entered on the substrate surface, when the haze value is calibrated by using the standard sample and the sample having the standard particles applied thereto is used as the standard sample, the haze measurement accuracy can be improved.

Here, it is preferable that the haze value is obtained by monitoring aging of the scattering light intensity of the light which is entered on a surface of the standard sample, and by changing a conversion rate of the haze value based on a change rate of the scattering light intensity of the standard sample.

When the haze value is obtained in this manner, a measurement accuracy of the haze can be effectively improved.

Here, it is preferable to calibrate the haze values of a plurality of particle counter apparatuses by measuring the scattering light intensity of the standard sample by the plurality of particle counter apparatuses and by determining a correction coefficient of the haze value based on measured values of the scattering light intensity of the standard sample.

When the haze values of the plurality of particle counter apparatuses are calibrated in this manner, a measurement accuracy of the haze when the plurality of particle counter apparatuses are used can be improved.

The present invention will now be more specifically described hereinafter with reference to experimental examples, but the present invention is not restricted thereto.

EXPERIMENTAL EXAMPLE 1

Aging of a median value of scattering light intensity detected from a wafer having PSL (polystyrene latex) standard particles (a particle diameter: 0.12 µm) applied thereto and a PSL standard particle size after conversion were measured. The measurement was performed by using the same particle counter apparatus. FIGS. 4(a) and (b) show results. Here, FIG. 4(a) shows aging of the median value of the scattering light intensity, and FIG. 4(b) shows aging of the PSL standard particle size after conversion.

EXPERIMENTAL EXAMPLE 2

Aging of a haze value detected from a specific position on the wafer used in Experimental Example 1 was measured. Here, in Experimental Example 2, scattering light from standard particles was simulatively regarded as the scattering light from the haze, and the haze was measured. The measurement was carried out by using the same particle counter apparatus as that used in Experimental Example 1. FIG. 4(a) shows a result.

As can be understood from FIG. 4(a), the median value of the scattering light intensity produced from the PSL standard particles of one size falls with time. As can be understood from FIG. 4(c), the haze value also simultaneously falls. However, in regard to the PSL standard particle size after conversion, as shown in FIG. 4(b), when the scattering light intensity falls and its change exceeds a fixed value, since a conversion value is changed such that the PSL standard particle size after conversion does not vary, aging of the PSL standard particle size after conversion is relatively small.

In this case, the median value of the scattering light intensity varies due to aging of the particle counter apparatus. As the aging of the apparatus, for example, there are a reduction in output of laser light, a reduction in sensitivity of a detector, and the like.

As to the particle size, when the calibration is performed with the use of the scattering light intensity and the standard particle size, the particles of the same size can be output as the same size even if a situation of the apparatus changes. On the other hand, according to the results of Experimental Examples 1 and 2, it was confirmed that monitoring the aging of the median value of the intensity of the scattering light produced from the standard particles of a known size enables indirectly monitoring the aging of the haze value.

Likewise, when a variation in median value of the intensity of the scattering light produced from the standard particles of a known size between the particle counter apparatuses is obtained, a variation in haze value between the particle counter apparatuses can be indirectly obtained.

EXAMPLES

The present invention will now be specifically described hereinafter with reference to examples, but the present invention is not restricted thereto.

Example 1

In a particle counter apparatus using scattering light, aging of a median value of intensity of the scattering light produced from a wafer having PSL standard particles of a particle diameter of 0.12 µm applied thereto (a standard sample) was monitored, and the median value of the intensity of the scattering light was 0.90-fold. At this time, multiplying a conversion rate of a haze value by 1.11 enabled obtaining a haze value to which offset of aging of the particle counter apparatus was reflected.

Example 2

In each of two particle counter apparatuses using scattering light (which will be referred to as an "apparatus A" and an "apparatus B" hereinafter, respectively), a median value of intensity of the scattering light produced from a wafer having PSL standard particles of a particle diameter of 0.12 µm applied thereto (a standard sample) was obtained. The median value of the intensity of the scattering light in the apparatus B was 1.20 times the median value of the scattering light in the apparatus A. At this time, determining a correction value of a haze value measured by the apparatus B as 0.83 times enabled obtaining a haze value to which offset of a fluctuation between the particle counter apparatuses was reflected.

It is to be noted that the present invention is not restricted to the foregoing embodiment. The foregoing embodiment is an illustrative example, and any example which has substantially the same structure and exerts the same functions and effects as the technical concept described in claims of the present invention is included in the technical scope of the present invention.

The invention claimed is:

1. A method for evaluating a haze of a substrate surface by a particle counter apparatus using scattering light, the substrate being an object to be evaluated,
the method comprising calibrating a haze value with the use of a standard sample for calibration at the time of obtaining the haze value of the substrate surface from scattering light intensity of light which is entered on the substrate surface, wherein
a sample in which standard particles are applied to a wafer is used as the standard sample,
the haze value is obtained by monitoring aging of the scattering light intensity of the light which is entered on a surface of the standard sample, and by changing a conversion rate of the haze value based on a change rate of the scattering light intensity of the standard sample, the standard sample is a sample having standard particles, which have a predetermined size applied thereto, and
the calibration of the haze value is performed such that a median value of the measured actual scattering light intensity is compared with a median value which is an initial value of the actual scattering light intensity when the standard sample is formed, and the haze value is calibrated based on a deviation from the initial value.

2. The method for evaluating a haze according to claim 1, wherein the haze values of a plurality of particle counter apparatuses are calibrated by measuring the scattering light intensity of the standard sample with using the plurality of particle counter apparatuses and by determining a correction coefficient of the haze value based on measured values of the scattering light intensity of the standard sample.

* * * * *